United States Patent [19]

Lammens et al.

[11] Patent Number: 4,957,922

[45] Date of Patent: Sep. 18, 1990

[54] INFUSION SOLUTIONS OF 1-CYCLOPROPYL-6-FLUORO-1,4-DIHYDRO-4-OXO-7-(1-PIPERAZINYL)-QUINOLINE-3-CARBOXYLIC ACID

[75] Inventors: Robert F. Lammens, Leverkusen; Hans F. Mahler, Colonge; Peter Serno, Colonge, all of Fed. Rep. of Germany

[73] Assignee: Bayer Aktiengesellschaft, Leverkusen, Fed. Rep. of Germany

[21] Appl. No.: 329,922

[22] Filed: Mar. 29, 1989

Related U.S. Application Data

[63] Continuation of Ser. No. 917,467, Oct. 10, 1986, abandoned.

[30] Foreign Application Priority Data

Oct. 24, 1985 [DE] Fed. Rep. of Germany ....... 3537761

[51] Int. Cl.$^5$ ............................................. A61K 31/495
[52] U.S. Cl. .................................................. 514/255
[58] Field of Search ......................................... 514/255

[56] References Cited

FOREIGN PATENT DOCUMENTS 0067666 12/1982 European Pat. Off. .

OTHER PUBLICATIONS

Chemical Abstracts 102: No. 21, May 27, 1985, p. 11.
Chemical Abstracts, vol. 103, No. 17, Oct. 28, 1985, p. 19.
Chemical Abstracts, vol. 105, No. 11, Sep. 15, 1986, p. 10.

*Primary Examiner*—Jerome D. Goldberg
*Attorney, Agent, or Firm*—Sprung Horn Kramer & Woods

[57] ABSTRACT

An aqueous infusion solution containing 0.015 to 0.5 g of 1-cyclopropyl-6-fluoro-1,4-dihydro-4-oxo-7-(1-piperazinyl)-quinoline-3-carboxylic acid per 100 ml of aqueous solution and an amount of at least one physiologically tolerated acid which suffices to dissolve the active compound.

13 Claims, No Drawings

INFUSION SOLUTIONS OF 1-CYCLOPROPYL-6-FLUORO-1,4-DI-HYDRO-4-OXO-7-(1-PIPERAZINYL)-QUINOLINE-3-CARBOXYLIC ACID

This is a continuation of application Ser. No. 917,467, filed Oct. 10, 1986, now abandoned.

The invention relates to both infusion solutions, which are ready for use, of 1-cyclopropyl-6-fluoro-1,4-dihydro-4-oxo-7-(1-piperazinyl)-quinoline-3-carboxylic acid (=ciprofloxacin, to be designated active compound in the text which follows) and other presentations, which, before administration, are converted into infusion solutions of this type. The invention likewise relates to processes for the preparation of the infusion solutions and to their use for the therapeutic treatment of the human or animal body.

Solutions of lactic acid salts of piperazinylquinoline- and piperazinyl-azaquinolinecarboxylic acids are described in European Patent Application No. 84110474.8.

European Patent Application No. 81106511.9 relates to 1-cyclopropyl-6-fluoro-1,4-dihydro-4-oxo-7-(1-piperazinyl)-quinoline-3-carboxylic acid and its pharmaceutically utilizable salts.

The present invention relates to infusion solutions of 1-cyclopropyl-6-fluoro-1,4-dihydro-4-oxo-7-(1-piperazinyl)-quinoline-3-carboxylic acid (=ciprofloxacin) which contain 0.015 to 0.5 g of the active compound per 100 ml of aqueous solution and an amount of a physiologically tolerated acid which suffices to dissolve the active compound and to stabilize the solution and, where appropriate, customary formulating auxiliaries.

In addition to the active compound, water and other customary formulating auxiliaries, the infusion solutions according to the invention preferably contain an amount, which suffices to dissolve the active compound and to stabilize the solution, of one or more acid(s) from the group comprising hydrochloric acid, methanesulphonic acid, propionic acid, succinic acid, glutaric acid, citric acid, fumaric acid, maleic acid, tartaric acid, glutamic acid, gluconic acid, glucuronic acid, galacturonic acid, ascorbic acid, phosphoric acid, adipic acid, hydroxyacetic acid, sulphuric acid, nitric acid, acetic acid, malic acid, L-aspartic acid and lactic acid.

Lactic acid and hydrochloric acid or mixtures of hydrochloric acid and lactic acid are particularly preferred.

Furthermore preferred are infusion solutions which contain 0.015 to 0.5 g of the active compound per 100 ml of aqueous solution and, depending on the active compound concentration, up to 5.0 mols, in particular 0.9 to 5.0 mols, and particularly preferably 1.04 to 2.20 mols, relative to 1 mol of active compound, of one or more physiologically tolerated acids, and where several acids are present their total content does not exceed the amount of 5.0 mols, relative to 1 mol of active compound.

Moreover, the invention preferably relates to infusion solutions which contain 0.015 to 0.5 g of the active compound per 100 ml of aqueous solution and up to 5.0 mols, relative to 1 mol of active compound, of lactic acid. The amounts of lactic acid in this connection are preferably 0.99 to 1.50 mols, in particular 1.04 to 1.40 mols, relative to 1 mol of active compound, of lactic acid. Infusion solutions of the active compound which contain 1.12 to 1.24 mols, relative to 1 mol of active compound, of lactic acid are particularly advantageous.

The infusion solutions according to the invention can also be modified in such a way that they contain up to 0.5 g of the active compound per 100 ml of aqueous solution and up to 1 mol, relative to 1 mol of active compound, of lactic acid, together with another physiologically tolerated acid, with the proviso that the total amount of acid is, depending on the active compound concentration, more than 0.9 mol but does not exceed 5.0 mol, relative to 1 mol of active compound.

The minimum amount of acid necessary per mol of active compound for the dissolution depends on the active compound concentration and the acid(s) used, and thus is not constant. However, within the limits according to the invention it can be determined by simple experiments. Furthermore, it should be noted that the data in the amounts of acid relate only to the amounts which, according to generally known chemical laws, are not converted by the addition of bases into the corresponding salt(s). Dissociation of the acids was left out of account in the data on the amounts so that they relate to the amount of dissociated and undissociated acid.

The lactic acid used in the formulations has a content of less than 25% (w/w), specifically for reasons of processing technology. The use of concentrated lactic acid—for example a 90% strength (w/w) product—gives rise to difficulties when the pH of the formulations according to the invention is to be adjusted after addition of the lactic acid—for example with hydrochloric acid or sodium hydroxide solution—with the objective that the adjusted pH remains constant, or changes only inconsiderably, during the remainder of the preparation process (such as, for example, a heat treatment at about 120° C. for about 20 min) and/or during storage.

The infusion solutions according to the invention can also contain other formulating aids such as thickeners, resorbents, light-protection agents, absorption inhibitors, crystallization accelerators, absorption accelerators, crystallization retardants, complexing agents, antioxidants, isotonicizing agents and/or euhydrogenating agents.

The osmolality of the infusion solutions is 0.20 to 0.70 Osm/kg, preferably 0.26 to 0.39 Osm/kg and is adjusted by isotonicizing agents such as NaCl, sorbitol, mannitol, glucose, sucrose, xylitol, fructose and glycerol or mixtures of such substances. Where appropriate, it is also possible to use for this substances which are contained in conventional commercially available infusion vehicle solutions.

The customary infusion vehicle solutions include infusion solutions with the addition of electrolytes without carbohydrates, such as sodium chloride solution, Ringer lactate solution and the like, and those with carbohydrates, as well as solutions for supplying amino acids, in each case with and without a carbohydrate content. Examples of infusion vehicle solutions of these types are listed in the Rote Liste 1985, list of finished pharmaceuticals of the members of the German Association of the Pharmaceutical Industry, Editio Cantor, Aulendorf/Württ.

Preferred infusion solutions are those which, apart from water, active compound and other formulating auxiliaries, contain an amount of sodium chloride, or other auxiliaries customary for isotonicizing, such that the solution is in a form which is isotonic, or slightly hypo- or hypertonic, with the tissue fluid in the human or animal body.

The infusion solutions according to the invention have a pH of 3.0 to 5.2. pH values from 3.6 to 4.7 and 3.9 to 4.5 are preferred. pH values in the range from 4.1 to 4.3 are very particularly preferred.

A very particularly preferred embodiment of the invention comprises infusion solutions which, apart from active compound, water and other formulating auxiliaries, contain, depending on the amount of active compound, 0.99 to 1.50 mols, preferably 1.04 to 1.40 mols, of lactic acid and 0.0 to 0.80 mol of hydrochloric acid (in each case relative to 1 mol of active compound), and, relative to 100 ml of solution, 0.6 to 2.2 g of NaCl, preferably 0.75 to 1.20 g, in particular 0.85 to 0.95 g of NaCl. The solutions thus obtained have osmolalities which differ according to the amount of sodium chloride and the active compound concentration. The osmolalities relating to the amounts of sodium chloride listed above are 0.2 to 0.7, 0.26 to 0.39 and 0.28 to 0.32 Osm/kg of solution respectively. Corresponding values can also be adjusted using other isotonicizing agents or mixtures thereof, as indicated above. Depending on the active compound and acid concentration, small differences from these osmolalities are perfectly possible.

The infusion solutions according to the invention can be in the form of dosage units, suitable for infusion, with removable contents of 40 to 600 ml, preferably 50 to 120 ml.

However, the invention also relates to lyophilizates which have been prepared by customary techniques and which are converted into the infusion solutions according to the invention by dissolution in solvents suitable for this purpose—such as, for example, conventional infusion vehicle solutions. Lyophilizates of this type can be obtained by freeze-drying of various starting solutions such as, for example, the infusion solutions according to the invention. It is likewise possible to freeze-dry considerably more dilute solutions as well as considerably more concentrated solutions than the infusion solutions according to the invention.

The lyophilizates can be prepared both by freeze-drying in the final container such as, for example, in a bottle or ampule made of glass or plastic, and by bulk freeze-drying combined with dispensing the lyophilizate into a container suitable for this purpose, which takes place at a later time.

The dissolution of the lyophilizate before the administration can be brought about both by addition of a solution, which is suitable for this purpose, into the container containing the lyophilizate and by addition of the lyophilizate to a suitable solution, or by a combination of procedures of these types.

The composition of the lyophilizates can likewise vary very widely, depending on the composition of the solution which is used for the dissolution.

It can vary from pure active compound to a lyophilizate which contains all the constituents which are to be administered, apart from water.

The invention likewise relates to combinations of lyophilizates with solutions containing active compound, which are converted into the infusion solutions according to the invention before the administration.

The invention also includes concentrates and suspensions which are converted into the solutions according to the invention before the administration.

It is possible in this context for these concentrates and suspensions to have various compositions. One possibility would be that which requires merely the addition of water for dilution or dissolution in order to prepare the infusion solutions according to the invention.

This invention relates to all combinations of concentrates and/or suspensions and to solutions which are necessary for dilution or dissolution and which result in the solutions according to the invention.

The invention also relates to other presentations or combinations of presentations which finally result in the infusion solutions according to the invention—and this irrespective of the procedure.

The containers into which lyophilizates, concentrates and other presentations such as, for example, suspensions, are dispensed can consist both of glass and of plastic. In this connection, the container materials can contain substances which confer a particular protection on the contents, such as, for example, a protection from light or a protection from oxygen.

The present invention additionally relates to a process for the preparation of infusion solutions, containing 0.015 to 0.5% by weight of 1-cyclopropyl-6-fluoro-1,4-dihydro-4-oxo-7-(1-piperazinyl)-quinoline-3-carboxylic acid (=ciprofloxacin). This process comprises mixing a suitable amount of the active compound, where appropriate in the form of a salt, such as an alkali metal or alkaline earth metal salt or addition salt, of a hydrate or of a hydrate of the salt, or in the form of mixtures of these salts or hydrates, with the amount of a physiologically tolerated acid or of a mixture of several physiologically tolerated acids which, in relation to the amount which just suffices to dissolve the active compound or its salts or hydrates, represents an excess preventing separation out of the active compound, adding, where appropriate, formulating auxiliaries, and making up with water or a customary infusion vehicle solution in such a manner that the concentration of the active compound is adjusted to the range from 0.015 to 0.5 g. In this connection, it has to be remembered that when the alkali metal or alkaline earth metal salts of the active compound are used the amounts of acid which are mentioned above as being necessary for dissolution contain the amount which is needed to neutralize the active compound anion, and that when addition salts are used a part of the amounts of acid necessary is already present in the active compound salt which is to be used.

Furthermore, care has to be taken in the preparation that the solution complies with the properties relating to pH, amounts of acid and osmolalities which have already been detailed.

In the case where the active compound is used in the salt form, it is possible and expedient to use an acid whose anion corresponds to the anion of the active compound salt or salt hydrate.

Where appropriate, the active compound is suspended in water, and up to 5 mols, relative to 1 mol of active compound, of lactic acid are added, and then, where appropriate, another physiologically tolerated acid or a mixture of such acids, in particular hydrochloric acid, is added, with the proviso that the total amount of acid does not exceed 5.0 mols, relative to 1 mol of active compound, but does exceed 0.9 mol, relative to 1 mol of active compound, and then, where appropriate, further formulating auxiliaries are added, in particular NaCl, which is also, where appropriate, produced by a neutralization reaction in the formulation mixture, and the desired active compound concentration is adjusted by making up with water.

The pH of the infusion solutions according to the invention can be adjusted with (physiologically) tolerated acids and/or bases to the abovementioned values, that is to say 3.0 to 5.2, in particular 3.6 to 4.7.

To speed up the preparation process, in particular the dissolution of solid components, it is possible gently to heat the solutions, or only a part thereof, preferably to temperatures between 20° C. and 80° C.

It has been possible particularly economically to prepare the solutions according to the invention via concentrated solutions. For this purpose, the amount of active compound necessary for a batch was dissolved with the major amount of acid necessary for the complete batch (for example >95% relative to the molar basis) in a little water—where appropriate with heating. This concentrate was then subsequently diluted. After dilution, any other auxiliaries—such as, for example, sodium chloride for isotonicizing—were added, as were the amounts of acid which were still lacking, where appropriate.

The infusion solutions according to the invention are used for the therapeutic treatment of the human or animal body.

The infusion solutions according to the invention have a low toxicity and a broad spectrum of anti-bacterial activity against Gram-positive and Gram-negative microbes, in particular against Enterobacteriaceae; especially including those which are resistant to various antibiotics such as, for example, penicillins, cephalosporins, aminoglycosides, sulphonamides and tetracyclines.

These valuable properties make it possible to use them in medicine.

The infusion solutions according to the invention are active against a very broad spectrum of microorganisms. They can be used to combat Gram-negative and Gram-positive bacteria and bacteria-like microorganisms and to prevent, ameliorate and/or heal illnesses caused by these pathogens.

The infusion solutions according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systemic illnesses caused by the following pathogens or by mixtures of the following pathogens can be treated and/or prevented:

Gram-positive cocci, for example Staphylococci (*Staph. aureus, Staph. epidermidis*) and Streptococci (*Strept. agalactiae, Strept. faecalis, Strept. pneumoniae, Strept. pyogenes*); Gram-negative cocci (*Neisseria gonorrhoeae*) and Gram-negative rods such as Enterobacteriaceae, for example *Escherichia coli, Hamophilus influenzae*, Citrobacter (*Citrob. freundii, Citrob. divernis*), Salmonella and Shigella; furthermore Klebsiella (*Klebs. pneumoniae, Klebs. oxytoca*), Enterobacter (*Ent. aerogenes, Ent. agglomerans*), Hafnia, Serratia (*Serr. marcescens*), Proteus (*Pr. mirabilis, Pr. rettgeri, Pr. vulgaris*), Providencia, Yersinia, and the genus Acinetobacter. Furthermore, the anti-bacterial spectrum covers the genus Pseudomonas (*Ps. aeruginosa, Ps. maltophilia*) and strictly anaerobic bacteria such as, for example, Bacteroides fragilis, representatives of the genus Peptococcus, Peptostreptococcus and the genus Clostridium; furthermore Mycoplasmas (*M. pneumoniae, M. hominis, M. urealyticum*) as well as Mycobacteria, for example *Mycobacterium tuberculosis*.

The above list of pathogens is purely illustrative and is in no way to be interpreted as restrictive. The following may be mentioned as examples of illnesses which are caused by the said pathogens or mixed infections and can be prevented, ameliorated or healed by the compounds according to the invention:

Infectious illnesses in humans such as, for example, otitis, pharyngitis, pneumonia, peritonitis, pyelonephritis, cystitis, endocarditis, systemic infections, bronchitis (acute and chronic), septic infections, illnesses of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmon, wound infections, infected burns, burns, infections in the mouth, infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

Apart from humans, it is also possible to treat bacterial infections in other species. The following may be mentioned as examples: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis.

It is likewise possible to treat bacterial illnesses in the rearing and maintenance of productive and ornamental fishes, the antibacterial spectrum extending beyond the pathogens mentioned above to further pathogens such as, for example, Pasteurella, Brucella, Campylobacter, Listeria, Erysipelothrix, Corynebacteria, Borellia, Treponema, Nocardia, Rickettsia and Yersinia.

EXAMPLES

The molar ratio—abbreviated to R—stated in the examples which follow always relates to the substance which is mentioned first in the relevant example.

| Examp. No. | Formulation | | | Micromole | R |
|---|---|---|---|---|---|
| 1 | Ciprofloxacin | | 90 mg | 272 | 1.00 |
| | Lactic acid 20% (w/w) | | 144.3 mg | 320 | 1.18 |
| | Hydrochloric acid | | 1.5 mg | 48 | 0.15 |
| | Sodium chloride | | 5.4 g | — | — |
| | Water | ad | 600.0 ml | | |
| | | pH: | approx. 4.3 | | |
| | | Osm: | approx. 0.29 Osm/kg | | |

-continued

| Examp. No. | Formulation | | | Micromole | R |
|---|---|---|---|---|---|
| 2 | Ciprofloxacin | | 150 mg | 453 | 1.00 |
| | Lactic acid 10% (w/w) | | 558 mg | 658 | 1.37 |
| | Hydrochloric acid | | 7.8 mg | 214 | 0.47 |
| | Glucose | | 30.0 g | — | — |
| | Water | ad | 600.00 ml | — | — |
| | | pH: | approx. 3.7 | | |
| | | Osm: | approx. 0.29 Osm/kg | | |
| 3 | Ciprofloxacin | | 100 mg | 302 | 1.00 |
| | Lactic acid 25% (w/w) | | 629 mg | 1745 | 5.78 |
| | 2 M NaOH solution | | 0.177 ml | 354 | 1.17 |
| | Fructose | | 20.0 g | — | |
| | Water | ad | 400.0 ml | — | |
| | | pH: | 3.6 a 3.7 | | |
| | | Osm: | 0.29 Osm/kg | | |
| 4 | Ciprofloxacin | | 75 mg | 226 | 1.00 |
| | 1 M hydrochloric acid | | 0.203 ml | 203 | 0.90 |
| | Sodium chloride | | 4.5 g | — | — |
| | Water | ad | 500 ml | — | — |
| | | pH: | 5.2 | | |
| | | Osm: | 0.29 Osm/kg | | |
| 5 | Ciprofloxacin lactate | | 254 mg | 604 | 1.00 (containing an equimolar amount of lactic acid) |
| | Lactic acid 5% (w/w) | | 400 mg | 222 | 1.00 |
| | Hydrochloric acid | | 10.4 mg | 285 | 0.47 |
| | Sodium chloride | | 1.8 g | | |
| | Glucose | | 10.0 g | | |
| | Water | ad | 400 ml | | |
| | | pH: | 3.7 | | |
| | | Osm: | 0.29 Osm/kg | | |
| 6 | Ciprofloxacin.5$H_2O$ | | 254 mg | 604 | 1.00 |
| | Lactic acid 2% (w/w) | | 2740 mg | 609 | 1.008 |
| | Sodium chloride | | 3.6 g | — | — |
| | Water | ad | 400 ml | — | — |
| | | pH: | 5.2 | | |
| | | Osm: | 0.29 Osm/kg | | |
| 7 | Ciprofloxacin acetate | | 118 mg | 302 | 1.00 (containing an equimolar amount of acetic acid) |
| | Acetic acid | | 3.6 mg | 60 | 0.20 |
| | Lactic acid 10% (w/w) | | 272 mg | 302 | 1.00 |
| | Sorbitol | | 10.0 g | — | — |
| | Water | ad | 200.0 ml | | |
| | | pH: | 4.7 | | |
| | | Osm: | 0.30 Osm/kg | | |
| 8 | Ciprofloxacin | | 200 mg | 604 | 1.00 |
| | Propionic acid | | 54 mg | 724 | 1.20 |
| | Lactic acid 20% (w/w) | | 136 mg | 604 | 1.00 |
| | Glucose | | 20.0 g | | |
| | Water | ad | 400.0 ml | | |
| | | pH: | 4.7 | | |
| | | Osm: | 0.3 Osm/kg | | |
| 9 | Ciprofloxacin lactate.2$H_2O$ | | 345 mg | 755 | 1.00 (containing an equimolar amount of lactic acid) |
| | Lactic acid 20% (w/w) | | 1822 mg | 4045 | 5.36 |
| | 0.2 M NaOH | | 5.25 ml | 1050 | 1.39 |
| | Sorbitol | | 5.0 g | — | — |
| | Water | ad | 250.0 ml | — | — |
| | | pH; | 3.6 | | |
| | | Osm: | 0.30 Osm/kg | | |
| 10 | Ciprofloxacin | | 200 mg | 604 | 1.00 |
| | Lactic acid 1% (w/w) | | 7440 mg | 826 | 1.37 |
| | 1 N hydrochloric acid | | 0.285 ml | 285 | 0.47 |
| | Mannitol | | 6.2 g | — | — |
| | Water | ad | 200 ml | | |
| | | pH: | 3.7 | | |
| | | Osm: | 0.37 Osm/kg | | |
| 11 | Ciprofloxacin | | 500 mg | 1509 | 1.00 |
| | Lactic acid 0.5% (w/w) | | 27182 mg | 1509 | 1.00 |
| | Sodium chloride | | 4.5 g | — | — |
| | Water | ad | 500 ml | | |
| | | pH: | 5.1 | | |
| | | Osm: | 0.29 Osm/kg | | |

-continued

| Examp. No. | Formulation | | | | Micromole | R |
|---|---|---|---|---|---|---|
| 12 | Ciprofloxacin | | 500 mg | 1509 | 1.00 | |
| | Lactic acid 5% (w/w) | | 2718 mg | 1509 | 1.00 | |
| | Glycerol | | 13.0 g | — | — | |
| | 1 M sodium chloride | | 1.885 ml | 1885 | 1.25 | |
| | Water | ad | 500 ml | | | |
| | | pH: | 3.0 | | | |
| | | Osm: | 0.29 Osm/kg | | | |
| 13 | Ciprofloxacin | | 100 mg | 302 | 1.00 | |
| | Lactic acid 0.1% (w/w) | | 32.2 g | 357 | 1.19 | |
| | Hydrochloric acid | | 1.6 mg | 45 | 0.15 | |
| | Glucose | | 4.48 g | — | — | |
| | Water | ad | 100 ml | | | |
| | | pH: | 4.2 | | | |
| | | Osm: | 0.26 Osm/kg | | | |
| 14 | Ciprofloxacin | | 50 mg | 151 | 1.00 | |
| | Lactic acid 10% (w/w) | | 160 mg | 178 | 1.18 | |
| | Sodium chloride | | 625 mg | | | |
| | Water | ad | 50 ml | | | |
| | | pH: | 4.4 | | | |
| | | Osm: | 0.40 Osm/kg | | | |
| 15 | Ciprofloxacin lactate.2H$_2$O | | 276 mg | 604 | 1.00 (containing an equimolar amount of lactic acid) | |
| | 1 M hydrochloric acid | | 0.151 ml | 151 | 0.25 | |
| | Fructose | | 17.2 g | — | — | |
| | Water | ad | 200.0 ml | | | |
| | | pH: | 4.2 | | | |
| | | Osm: | 0.50 Osm/kg | | | |
| 16 | Ciprofloxacin | | 500 mg | 1509 | 1.00 | |
| | Lactic acid 2% (w/w) | | 6727 mg | 1494 | 0.99 | |
| | Sorbitol | | 25.0 g | | | |
| | Water | ad | 500 ml | | | |
| | | pH: | 5.0 | | | |
| | | Osm: | 0.29 Osm/kg | | | |
| 17 | Ciprofloxacin lactate | | 127 mg | 302 | 1.00 (containing an equimolar amount of lactic acid) | |
| | Maleic acid | | 42 mg | 364 | 1.20 | |
| | Mannitol | | 5.0 g | | | |
| | Water | ad | 100.0 ml | | | |
| | | pH: | 3.1 | | | |
| | | Osm: | 0.30 Osm/kg | | | |
| 18 | Ciprofloxacin | | 200 mg | 604 | 1.00 | |
| | Lactic acid 20% (w/w) | | 297 mg | 659 | 1.09 | |
| | Glutaric acid | | 40 mg | 302 | 0.50 | |
| | Fructose | | 10.0 g | | | |
| | Water | ad | 200 ml | | | |
| | | pH: | 4.3 | | | |
| | | Osm: | 0.30 Osm/kg | | | |
| 19 | Ciprofloxacin | | 200 mg | 604 | 1.00 | |
| | Lactic acid 10% (w/w) | | 566 mg | 628 | 1.04 | |
| | Sodium chloride | | 0.9 g | — | — | |
| | Water | ad | 100.0 ml | | | |
| | | pH: | 4.9 | | | |
| | | Osm: | 0.29 Osm/kg | | | |
| 20 | Ciprofloxacin | | 400 mg | 1207 | 1.00 | |
| | Lactic acid 20% (w/w) | | 745 mg | 1654 | 1.37 | |
| | Hydrochloric acid | | 20.8 mg | 570 | 0.47 | |
| | Sodium chloride | | 1800 mg | | | |
| | Water | ad | 200 ml | | | |
| | | pH: | 3.7 | | | |
| | | Osm: | 0.29 Osm/kg | | | |
| 21 | Ciprofloxacin.5H$_2$O | | 509 mg | 1207 | 1.00 | |
| | Lactic acid 5% (w/w) | | 2568 mg | 1425 | 1.18 | |
| | Hydrochloric acid | | 6.6 mg | 180 | 0.15 | |
| | Glucose | | 5.0 g | — | — | |
| | Water | ad | 200 ml | | | |
| | | pH: | 4.2 | | | |
| | | Osm: | 0.30 Osm/kg | | | |
| 22 | Ciprofloxacin.5H$_{Ciprofloxacin.5}$ $_2$O | | 254 mg | 604 | 1.00 | |
| | Lactic acid 25% (w/w) | | 257 mg | 713 | 1.18 | |
| | Hydrochloric acid | | 3.3 mg | 90 | 0.15 | |
| | Sorbitol | | 5.0 g | | | |
| | Water | ad | 100.0 ml | | | |
| | | pH: | 4.2 | | | |
| | | Osm: | 0.30 Osm/kg | | | |

-continued

| Examp. No. | Formulation | | | Micromole | R |
|---|---|---|---|---|---|
| 23 | Ciprofloxacin | | 200 mg | 604 | 1.00 |
| | Lactic acid 20% (w/w) | | 322 mg | 715 | 1.18 |
| | 1 M hydrochloric acid | | 0.090 ml | 90 | 0.15 |
| | Sodium chloride | | 0.9 g | | |
| | Water | ad | 100.0 ml | | |
| | | pH: | 4.2 | | |
| | | Osm: | 0.30 Osm/kg | | |
| 24 | Ciprofloxacin | | 100 mg | 302 | 1.00 |
| | Lactic acid 0.4% (w/w) | | 7407 mg | 329 | 1.09 |
| | 1 M hydrochloric acid | | 3.42 ml | 3420 | 11.32 |
| | 2 M sodium hydroxide solution | | 1.71 ml | 3420 | 11.32 |
| | Sodium chloride | | 0.25 g | | |
| | Water | ad | 50.0 ml | | |
| | | pH: | 4.7 | | |
| | | Osm: | Osm/kg | | |
| 25 | Ciprofloxacin | | 200 mg | 604 | 1.00 |
| | Lactic acid 10% (w/w) | | 642 mg | 713 | 1.18 |
| | Hydrochloric acid | | 3.3 mg | 90 | 0.15 |
| | Sodium chloride | | 0.855 g | | |
| | Water | ad | 100.0 ml | | |
| | | pH: | 4.2 | | |
| | | Osm: | 0.29 Osm/kg | | |
| 26 | Ciprofloxacin.5H$_2$O | | 254 mg | 604 | 1.00 |
| | Lactic acid 20% (w/w) | | 322 mg | 715 | 1.18 |
| | 0.1 M hydrochloric acid | | 0.90 ml | 90 | — |
| | Sodium chloride | | 0.945 g | — | — |
| | Water | ad | 100.0 ml | | |
| | | pH: | 4.2 | | |
| | | Osm: | 0.32 Osm/kg | | |
| 27 | Ciprofloxacin lactate.2H$_2$O | | 276 mg | 604 | 1.00 (containing an equimolar amount of lactic acid) |
| | Lactic acid 0.5% (w/w) | | 2000 mg | 111 | 0.18 |
| | Hydrochloric acid | | 3.3 mg | 90 | 0.15 |
| | Xylitol | | 4.2 g | — | — |
| | Water | ad | 100.0 ml | | |
| | | pH: | 4.2 | | |
| | | Osm: | 0.30 Osm/kg | | |
| 28 | Ciprofloxacin lactate | | 254 mg | 604 | 1.00 (containing an equimolar amount of lactic acid) |
| | Lactic acid 20% (w/w) | | 50 mg | 111 | 0.18 |
| | Hydrochloric acid | | 3.3 mg | 90 | 0.15 |
| | Fructose | | 6.0 g | | |
| | Water | ad | 100.0 ml | | |
| | | pH: | 4.2 | | |
| | | Osm: | 0.37 Osm/kg | | |
| 29 | Ciprofloxacin HCl.H$_2$O | | 232 mg | 604 | 1.00 (containing an equimolar amount of hydrochloric acid) |
| | Lactic acid 5% (w/w) | | 1288 mg | 715 | 1.18 |
| | 2 M sodium hydroxide solution | | 0.257 ml | 514 | 0.85 |
| | Sodium chloride | | 0.870 g | | |
| | Water | ad | 100 ml | | |
| | | pH: | 4.2 | | |
| | | Osm: | 0.30 Osm/kg | | |
| 30 | Ciprofloxacin Na (Sodium salt of ciprofloxacin | | 213 mg | 604 | 1.00 |
| | Lactic acid 10% (w/w) | | 744 mg | 826 | 1.37 |
| | Hydrochloric acid | | 32.4 mg | 888 | 1.47 |
| | Glucose | | 4.8 g | | |
| | Water | ad | 100.0 ml | | |
| | | pH: | 3.7 | | |
| | | Osm: | 0.30 Osm/kg | | |
| 31 | Calcium salt of ciprofloxacin | | 212 mg | 604 | 1.00 |
| | Lactic acid 2% (w/w) | | 3220 mg | 715 | 1.18 |
| | Hydrochloric acid | | 25.3 mg | 693 | 1.15 |
| | Glycerol | | 2.6 g | — | — |
| | Water | ad | 500.0 ml | | |
| | | pH: | 4.3 | | |
| | | Osm: | 0.30 Osm/kg | | |
| 32 | Potassium salt of ciprofloxacin | | 233 mg | 604 | 1.00 |
| | Lactic acid 20% (w/w) | | 277 mg | 615 | 1.018 |
| | 0.1 M hydrochloric acid | | 8.86 ml | 886 | 1.47 |

| Examp. No. | Formulation | | | Micromole | R |
|---|---|---|---|---|---|
| | Glucose | | 5.0 g | | |
| | Water | ad | 100.0 ml | | |
| | | pH: | 4.6 | | |
| | | Osm: | 0.30 Osm/kg | | |
| 33 | Ciprofloxacin lactate.2H$_2$O | | 276 mg | 604 | 1.00 (containing an equimolar amount of lactic acid) |
| | Lactic acid 10% (w/w) | | 2915 mg | 3236 | 5.36 |
| | 0.1 M sodium hydroxide solution | | 8.40 ml | 840 | 1.39 |
| | Glucose | | 5.0 g | | |
| | Water | ad | 100.0 ml | | |
| | | pH: | 3.6 | | |
| | | Osm: | 0.3 Osm/kg | | |
| 34 | Ciprofloxacin HCl (Hydrochloride of ciprofloxacin) | | 222 mg | 604 | 1.00 (containing an equimolar amount of hydrochloric acid) |
| | Lactic acid 0.1% (w/w) | | 55.4 g | 615 | 1.018 |
| | 2 M sodium hydroxide solution | | 0.302 ml | 604 | 1.00 |
| | Hydrochloric acid | | 10.4 mg | 284 | 0.47 |
| | Sodium chloride | | 0.90 g | — | — |
| | Water | ad | 100.0 ml | | |
| | | pH: | 4.6 | | |
| | | Osm: | 0.30 Osm/kg | | |
| 35 | Ciprofloxacin | | 200 mg | 604 | 1.00 |
| | Tartaric acid | | 91 mg | 604 | 1.00 |
| | Xylitol | | 4.2 g | | |
| | Water | ad | 100.0 ml | | |
| | | pH: | 3.6 | | |
| | | Osm: | 0.30 Osm/kg | | |
| 36 | Ciprofloxacin gluconate | | 159 mg | 302 | 1.00 (containing an equimolar amount of gluconic acid) |
| | Gluconic acid | | 12 mg | 62 | 0.20 |
| | Lactic acid 5% (w/w) | | 544 mg | 302 | 1.00 |
| | Glycerol | | 1.3 g | — | — |
| | Water | ad | 50.0 ml | | |
| | | pH: | 4.0 | | |
| | | Osm: | 0.30 Osm/kg | | |
| 37 | Ciprofloxacin | | 500 mg | 1509 | 1.00 |
| | Galacturonic acid | | 351 mg | 1811 | 1.20 |
| | Sorbitol | | 25.0 g | | |
| | Water | ad | 250.0 ml | | |
| | | pH: | 4.6 | | |
| | | Osm: | 0.3 Osm/kg | | |
| 38 | Ciprofloxacin.5H$_2$O | | 127 mg | 302 | 1.00 |
| | Ascorbic acid | | 41 mg | 366 | 1.21 |
| | Glucose | | 2.5 g | | |
| | Water | ad | 50 ml | | |
| | | pH: | 4.5 | | |
| | | Osm: | 0.30 Osm/kg | | |
| 39 | Ciprofloxacin | | 200 mg | 604 | 1.00 |
| | Adipic acid | | 106 mg | 724 | 1.20 |
| | Lactic acid 20% (w/w) | | 272 mg | | |
| | Fructose | | 5.0 g | | |
| | Water | ad | 100.0 ml | | |
| | | pH: | 4.1 | | |
| | | Osm: | 0.30 Osm/kg | | |
| 40 | Ciprofloxacin lactate | | 509 mg | 1207 | 1.00 (containing an equimolar amount of lactic acid) |
| | Hydroxyacetic acid | | 110 mg | 1448 | 1.20 |
| | Sodium chloride | | 1.8 g | | |
| | Water | ad | 200 ml | | |
| | | pH: | 4.0 | | |
| | | Osm: | 0.30 Osm/kg | | |
| 41 | Ciprofloxacin | | 200 mg | 604 | 1.00 |
| | Malic acid | | 81 mg | | |
| | Glucose | | 5.0 g | | |
| | Water | ad | 100.0 ml | | |
| | | pH: | 4.2 | | |
| | | Osm: | 0.30 Osm/kg | | |
| 42 | Ciprofloxacin | | 100 mg | 302 | 1.00 |

-continued

| Examp. No. | Formulation | | | Micromole | R |
|---|---|---|---|---|---|
| | L. aspartic acid | | 48 mg | 361 | 1.20 |
| | Fructose | | 2.5 g | | |
| | Water | ad | 50.0 ml | | |
| | pH: | | 4.5 | | |
| | Osm: | | 0.30 Osm/kg | | |
| 43 | Ciprofloxacin | | 100 mg | 302 | 1.00 |
| | Lactic acid 20% (w/w) | | 204 mg | 453 | 1.50 |
| | 0.1 M hydrochloric acid | | 2.11 ml | 211 | 0.70 |
| | Sorbitol | | 2.5 g | | |
| | Water | ad | 50.0 ml | | |
| | pH: | | 3.3 | | |
| | Osm: | | 0.30 Osm/kg | | |
| 44 | Ciprofloxacin.5H$_2$O | | 318 mg | 754 | 1.00 |
| | Lactic acid 25% (w/w) | | 1572 mg | 4363 | 5.78 |
| | 0.2 M sodium hydroxide solution | | 4.40 ml | 880 | 1.17 |
| | Mannitol | | 5.0 g | | |
| | Water | ad | 50.0 ml | | |
| | pH: | | 3.6 | | |
| | Osm: | | 0.35 Osm/kg | | |
| 45 | Ciprofloxacin | | 200 mg | 604 | 1.00 |
| | Lactic acid 15% (w/w) | | 496 mg | 826 | 1.37 |
| | 0.2 M hydrochloric acid | | 1.42 ml | 284 | 0.47 |
| | Glucose | | 5.00 g | | |
| | Water | ad | 40.0 ml | | |
| | pH: | | 3.7 | | |
| | Osm: | | 0.33 Osm/kg | | |
| 46 | Ciprofloxacin lactate.2H$_2$O | | 3858 mg | 7544 | 1.00 (containing an equimolar amount of lactic acid) |
| | Sodium chloride | | 4.5 g | — | — |
| | 1 M hydrochloric acid | | 0.754 ml | 754 | 0.10 |
| | Water | ad | 500 ml | | |
| | pH: | | 4.7 | | |
| | Osm; | | 0.30 Osm/kg | | |
| 47 | Ciprofloxacin | | 500 mg | 1509 | 1.00 |
| | Lactic acid 1% | | 14814 mg | 1645 | 1.09 |
| | Sodium chloride | | 0.45 g | | |
| | Water | ad | 100.0 ml | | |
| | pH: | | 4.7 | | |
| | Osm: | | 0.31 Osm/kg | | |
| 48 | Ciprofloxacin HCl.H$_2$O | | 244 mg | 604 | 1.00 (containing an equimolar amount of hydrochloric acid) |
| | Fructose | | 2.0 g | | |
| | Water | ad | 40.0 ml | | |
| | pH: | | 4.0 | | |
| | Osm: | | 0.30 Osm/kg | | |
| 49 | Ciprofloxacin lactate.2H$_2$O | | 359 mg | 754 | 1.00 (containing an equimolar amount of lactic acid) |
| | Lactic acid 20% (w/w) | | 2.6 mg | 69 | 0.09 |
| | Succinic acid | | 45 mg | 381 | 0.51 |
| | Sorbitol | | 2.5 g | | |
| | Water | ad | 50.0 ml | | |
| | pH: | | 4.2 | | |
| | Osm: | | 0.32 Osm/kg | | |
| 50 | Ciprofloxacin | | 500 mg | 1509 | 1.00 |
| | Lactic acid 10% (w/w) | | 1481 mg | 1644 | 1.09 |
| | Citric acid | | 159 mg | 757 | 0.50 |
| | Glucose | | 5.0 g | | |
| | Water | ad | 100.0 ml | | |
| | pH: | | 3.8 | | |
| | Osm: | | 0.33 Osm/kg | | |
| 51 | Ciprofloxacin lactate | 127 | mg 302 | | 1.00 (containing an equimolar amount of lactic acid) |
| | Ciprofloxacin fumarate | | 68 mg | 151 | 0.50 containing an equimolar amount of fumaric acid |
| | Ciprofloxacin | | 50 mg | 151 | 0.50 |

-continued

| Examp. No. | Formulation | | | | Micromole | R |
|---|---|---|---|---|---|---|
| | Lactic acid 20% | | 160 mg | | 356 | 1.18 |
| | Fructose | | 2.0 g | | | |
| | Water | ad | 40.0 ml | | | |
| | | pH: | 3.9 | | | |
| | | Osm: | 0.32 Osm/kg | | | |
| 52 | Ciprofloxacin | | 250 mg | | 754 | 1.00 |
| | L-glutamic acid | | 111 mg | | 754 | 1.00 |
| | Mannitol | | 3.5 g | | | |
| | Water | ad | 50.0 ml | | | |
| | | pH: | 4.6 | | | |
| | | Osm: | 0.42 Osm/kg | | | |
| 53 | Ciprofloxacin | | 500 mg | | 1509 | 1.00 |
| | 1 M hydrochloric acid | | 1.51 ml | | 1510 | 1.00 |
| | Glucose | | 12.5 g | | | |
| | Water | ad | 250 ml | | | |
| | | pH: | 4.0 | | | |
| | | Osm: | 0.32 Osm/kg | | | |
| 54 | Ciprofloxacin | | 500 mg | | 1509 | 1.00 |
| | Lactic acid 25% | | 641 mg | | 1780 | 1.18 |
| | Sodium chloride | | 0.0 g | | | |
| | Water | ad | 100.0 ml | | | |
| | | pH: | 4.5 | | | |
| | | Osm: | 0.30 Osm/kg | | | |
| 55 | Solution A | | | | | |
| | Ciprofloxacin lactate | | 127 mg | | 302 | 1.00 (containing an equimolar amount of lactic acid) |
| | Lactic acid 20% (w/w) | | 25 mg | | 56 | 0.19 |
| | Hydrochloric acid | | 1.6 mg | | 45 | 0.15 |
| | Sodium chloride | | 0.9 g | | | |
| | Water | ad | 100.0 ml | | | |
| | Solution B | | | | | |
| | Sodium chloride | | 2.25 g | | | |
| | Water | ad | 250 ml | | | |
| | Prepare the solution ready for use by mixing solution A and B | | | | | |
| 56 | Solution A | | | | | |
| | Solution A from Example 55 | | | | | |
| | Solution B | | | | | |
| | Sodium chloride | | 4.95 g | | | |
| | Water | ad | 550 ml | | | |
| | Prepare the solution ready for use by mixing solution A and B | | | | | |
| 57 | Solution A | | | | | |
| | Ciprofloxacin | | 100 mg | | 302 | 1.00 |
| | Lactic acid 6% (w/w) | | 537 mg | | 358 | 1.19 |
| | 0.1 M hydrochloric acid | | 0.45 ml | | 45 | 0.15 |
| | Sodium chloride | | 0.45 g | | | |
| | Water | ad | 50.0 ml | | | |
| | Solution B | | | | | |
| | Glucose | | 12.5 g | | | |
| | Water | ad | 250 ml | | | |
| | Prepare the solution ready for use by mixing solution A and B | | | | | |
| 58 | Solution A | | | | | |
| | Ciprofloxacin | | 100 mg | | 302 | 1.00 |
| | Lactic acid 2% (w/w) | | 1610 mg | | 358 | 1.19 |
| | Hydrochloric acid | | 1.6 mg | | 45 | |
| | Glucose | | 2.5 g | | | |
| | Water | ad | 50 ml | | | |
| | Solution B | | | | | |
| | Sodium chloride | | 900 mg | | | |
| | Water | ad | 100 ml | | | |
| | Prepare the solution ready for use by mixing solution A and B | | | | | |
| 59 | Solution A | | | | | |
| | Potassium salt of ciprofloxacin | | 223 mg | | 604 | 1.00 |
| | Lactic acid 20% (w/w) | | 277 mg | | 615 | 1.018 |
| | 0.1 M hydrochloric acid | | 8.86 ml | | 886 | 1.47 |
| | Glucose | | 5.0 g | | | |
| | Water | ad | 100.0 ml | | | |
| | Solution B | | | | | |
| | Ringer lactate solution | | 500 ml (for example Ringer lactate DAB 7 Braun Melsungen Rote Liste 1985 No. 51013) | | | |
| | Prepare solution ready for use by mixing solution A and B | | | | | |
| 60 | Solution A | | | | | |
| | Ciprofloxacin lactate.2H₂O | | 276 mg | | 604 | 1.00 (containing an |

-continued

| Examp. No. | Formulation | | | Micromole | R |
|---|---|---|---|---|---|
| | | | | | equimolar amount of lactic acid) |
| | Lactic acid 0.1% (w/w) | | 10.0 g | 111 | 0.18 |
| | Hydrochloric acid | | 3.3 mg | 90 | 0.15 |
| | Xylitol | | 4.2 g | | |
| | Water | ad | 100.0 ml | | |
| | Solution B | | | | |
| | Fructose | | 10.0 g | | |
| | Water | ad | 100.0 ml | | |
| | Prepare the solution ready for use by mixing solution A and B | | | | |
| 61 | Solution A | | | | |
| | Ciprofloxacin | | 200 mg | 604 | 1.00 |
| | Lactic acid 10% (w/w) | | 644 mg | 715 | 1.18 |
| | 0.1 M hydrochloric acid | | 0.90 ml | 90 | 0.15 |
| | Sodium chloride | | 0.9 g | | |
| | Water | ad | 100.0 ml | | |
| | Solution B | | | | |
| | Xylitol | | 12.5 g | | |
| | Water | ad | 250 ml | | |
| | Prepare the solution ready for use by mixing solution A and B | | | | |
| 62 | Solution A | | | | |
| | Ciprofloxacin | | 200 mg | 604 | 1.00 |
| | Lactic acid 1.5% (w/w) | | 4960 mg | 826 | 1.37 |
| | 0.1 M hydrochloric acid | | 2.84 ml | 284 | 0.47 |
| | Glucose | | 5.00 g | | |
| | Water | ad | 40.0 ml | | |
| | Solution B | | | | |
| | Glucose | | 5.0 g | | |
| | Water | ad | 100 ml | | |
| | Prepare the solution ready for use by mixing solution A and B | | | | |
| 63 | Solution A | | | | |
| | Ciprofloxacin | | 50 mg | 151 | 1.00 |
| | Lactic acid 20% (w/w) | | 393 mg | 872 | 5.77 |
| | 0.2 M sodium hydroxide solution | | 0.89 ml | 178 | 1.18 |
| | Water | ad | 5.0 ml | | |
| | Solution B | | | | |
| | Sorbitol | | 2.5 g | | |
| | Water | ad | 50.0 ml | | |
| | Prepare the solution ready for use by mixing solution A and B | | | | |
| 64 | Solution A | | | | |
| | Solution of Example 63 | | | | |
| | Solution B | | | | |
| | Glucose | | 5.0 g | | |
| | Water | ad | 100.0 ml | | |
| | Prepare the solution ready for use by mixing solution A and B | | | | |
| 65 | Solution A | | | | |
| | Ciprofloxacin | | 100 mg | 302 | 1.00 |
| | Lactic acid 10% (w/w) | | 372 mg | 413 | 1.37 |
| | Hydrochloric acid | | 5.2 mg | 142 | 0.47 |
| | Water | ad | 10.0 ml | | |
| | Solution B | | | | |
| | Sodium chloride | | 0.45 g | | |
| | Water | ad | 50.0 ml | | |
| | Prepare the solution ready for use by mixing solution A and B | | | | |
| 66 | Solution A | | | | |
| | Solution A from Example 65 | | | | |
| | Solution B | | | | |
| | Fructose | | 5.0 g | | |
| | Water | ad | 100.0 ml | | |
| | prepare the solution ready for use by mixing solution A and B | | | | |
| 67 | Solution A | | | | |
| | Solution A from Example 65 | | | | |
| | Solution B | | | | |
| | Ringer lactate solution: | | 250 ml (for example Ringer lactate DAB 7 manufactured by Braun Melsungen Rote Liste 1985 No. 51013) | | |
| | Prepare the solution ready for use by mixing solution A and B | | | | |
| 68 | Solution A | | | | |
| | Solution A from Example 65 | | | | |
| | Solution B | | | | |
| | Mannitol | | 25.0 g | | |
| | Water | ad | 500.0 ml | | |
| | Prepare the solution ready for use by mixing solution A and B | | | | |
| 69 | Solution A | | | | |

| Examp. No. | Formulation | | | Micromole | R |
|---|---|---|---|---|---|
| | Ciprofloxacin lactate | | 254 mg | 604 | 1.00 (containing an equimolar amount of lactic acid) |
| | Lactic acid 5% (w/w) | | 1188 mg | 659 | 1.09 |
| | 1 M hydrochloric acid | | 0.120 ml | 120 | 1.40 |
| | Water | ad | 20.0 ml | | |
| | Solution B | | | | |
| | Fructose | | 10.0 g | | |
| | Water | ad | 100.0 ml | | |
| | Prepare the solution ready for use by mixing solution A and B | | | | |
| 70 | Solution A | | | | |
| | Solution A from Example 69 | | | | |
| | Solution B | | | | |
| | Sodium chloride | | 2.25 g | | |
| | Water | ad | 250.0 ml | | |
| | Prepare the solution ready for use by mixing solution A and B | | | | |
| 71 | Solution A | | | | |
| | Solution A from Example 69 | | | | |
| | Solution B | | | | |
| | Ringer lactate solution | | 500 ml (for example Ringer lactate DAB 7 supplied by Braun Melsunger/ Rote Liste 1985 No. 51013) | | |
| 72 | Solution A | | | | |
| | Ciprofloxacin | | 250 mg | 754 | 1.00 |
| | Lactic acid 20% (w/w) | | 465 mg | 1032 | 1.37 |
| | 0.1 M hydrochloric acid solution | | 1.63 ml | 163 | 0.22 |
| | Sodium chloride | | 173 mg | | |
| | Water | | 25 ml | | |
| | Solution B | | | | |
| | Glucose | | 5.0 g | | |
| | Water | | 100.0 ml | | |
| | Prepare the solution ready for use by mixing solution A and B | | | | |
| 73 | Solution A | | | | |
| | Solution A from Example 72 | | | | |
| | Solution B | | | | |
| | Sodium chloride | | 2.25 g | | |
| | Water | | 250 ml | | |
| | Prepare the solution ready for use by mixing solution A and B | | | | |
| 74 | Solution A | | | | |
| | Ciprofloxacin lactate.2H$_2$O | | 276 mg | 604 | 1.00 (containing an equimolar amount of lactic acid) |
| | Lactic acid 10% (w/w) | | 20 mg | 22 | 0.037 |
| | 0.1 M hydrochloric acid solution | | 2.00 ml | 200 | 0.33 |
| | Water | | 4.0 ml | | |
| | Solution B | | | | |
| | Mannitol | | 5.0 g | | |
| | Water | | 100.0 ml | | |
| | Prepare the solution ready for use by mixing solution A and B | | | | |
| 75 | Solution A | | | | |
| | Solution A from Example 74 | | | | |
| | Solution B | | | | |
| | Glucose | | 25.0 g | | |
| | Water | ad | 250.0 ml | | |
| | Prepare the solution ready for use by mixing solution A and B | | | | |
| 76 | Solution A | | | | |
| | Solution A from Example 74 | | | | |
| | Solution B | | | | |
| | Sodium chloride | | 4.5 g | | |
| | Water | ad | 500.0 ml | | |
| | Prepare the solution ready for use by mixing solution A and B | | | | |
| 77 | Solution A | | | | |
| | Ciprofloxacin | | 100 mg | 302 | 1.00 |
| | Lactic acid 20% (w/w) | | 168 mg | 373 | 1.24 |
| | Water | ad | 1.00 ml | | |
| | Solution B | | | | |
| | Sodium chloride | | 0.45 g | | |
| | Water | ad | 50.0 ml | | |
| | Prepare the solution ready for use by mixing solution A and B | | | | |
| 78 | Solution A | | | | |
| | Solution A from Example 77 | | | | |

| Examp. No. | Formulation | | | Micromole | R |
|---|---|---|---|---|---|
| | Solution B | | | | |
| | Ringer lactate solution: | | 100 ml (for example Ringer lactate DAB 7 supplied by Braun Melsungen Rote Liste 1985 No. 51013) | | |
| | Prepare the solution ready for use by mixing solution A and B | | | | |
| 79 | Solution A | | | | |
| | Ciprofloxacin | | 200 mg | 604 | 1.00 |
| | Lactic acid 25% (w/w) | | 257 mg | 715 | 1.18 |
| | Water | ad | 1.00 ml | | |
| | Solution B | | | | |
| | Sodium chloride | | 0.9 g | | |
| | Water | ad | 100.0 ml | | |
| | Prepare the solution ready for use by mixing solution A and B | | | | |
| 80 | Solution A | | | | |
| | Ciprofloxacin | | 175 mg | 528 | 1.00 |
| | Lactic acid 20% (w/w) | | 300 mg | 667 | 1.26 |
| | Water | ad | 0.5 ml | | |
| | Solution B | | | | |
| | Glucose | | 2.5 g | | |
| | Water | ad | 50.0 ml | | |
| | Prepare this solution ready for use by mixing solution A and B | | | | |
| 81 | Solution A | | | | |
| | Ciprofloxacin | | 200 mg | 604 | 1.00 |
| | Lactic acid 20% (w/w) | | 322 mg | 715 | 1.18 |
| | Hydrochloric acid | | 3.3 mg | 90 | 0.15 |
| | Sodium chloride | | 0.9 g | | |
| | Water | ad | 100.0 ml | | |
| | Solution B | | | | |
| | Solution for supplying amino acids: | | 500 ml (for example Aminoplasmal LS-5 electrolyte-free, supplied by Braun Melsungen, Rote Liste 1985 No. 51238) | | |
| | Prepare the solution ready for use by mixing solution A and B | | | | |
| 82 | Solution A | | | | |
| | Ciprofloxacin | | 100 mg | 302 | 1.00 |
| | Lactic acid 2% (w/w) | | 1481 mg | 329 | 1.09 |
| | Phosphoric acid | | 16 mg | 165 | 0.50 |
| | Water | ad | 10.0 ml | | |
| | | pH: | 3.8 | | |
| | Solution B | | | | |
| | Sodium chloride | | 3.6 g | | |
| | Water | ad | 400 ml | | |
| | Prepare the solution ready for use by mixing Solution A and B | | | | |
| 83 | Solution A | | | | |
| | Ciprofloxacin lactate | | 254 mg | 604 | 1.00 (containing an equimolar amount of lactic acid) |
| | Lactic acid 0.5% (w/w) | | 979 mg | 54 | 0.09 |
| | Methanesulphonic acid | | 116 mg | 1208 | 2.00 |
| | 0.2 M sodium hydroxide solution | | 2.4 ml | 480 | 0.79 |
| | Water | ad | 20.0 ml | | |
| | | pH: | 3.8 | | |
| | Solution B | | | | |
| | Glucose | | 20.0 g | | |
| | Water | ad | 400.0 ml | | |
| | Prepare the solution ready for use by mixing solution A and B | | | | |
| 84 | Lyophilizate | | | | |
| | Ciprofloxacin | | 100 mg | 302 | 1.00 |
| | Solution | | | | |
| | Lactic acid 10% (w/w) | | 322 mg | 358 | 1.18 |
| | Hydrochloric acid | | 1.6 mg | 45 | 0.15 |
| | Sodium chloride | | 900 mg | | |
| | Water | ad | 100.0 ml | | |
| | Prepare solution ready for use by dissolving the lyophilizate in the solution | | | | |
| 85 | Lyophilizate | | | | |
| | Ciprofloxacin lactate | | 63.6 mg | 151 | 1.00 (containing an equimolar amount of lactic acid) |
| | Solution | | | | |
| | Lactic acid 0.005% (w/w) | | 10.87 g | 6 | 1.04 |
| | Sodium chloride | | 225 mg | | |
| | Water | ad | 25 ml | | |
| | Prepare solution ready for use by dissolving the lyophilizate in the solution | | | | |

-continued

| Examp. No. | Formulation | | | Micromole | R |
|---|---|---|---|---|---|
| 86 | Lyophilizate | | | | |
| | Ciprofloxacin lactate | 127 mg | | 302 | 1.00 (containing an equimolar amount of lactic acid) |
| | Lactic acid | 1.1 mg | | 12 | 0.04 |
| | Mannitol | 5.0 g | | | |
| | Solution | | | | |
| | Water | ad | 100.0 ml | | |
| | Prepare solution ready for use by dissolving the lyophilizate in the solution | | | | |
| 87 | Lyophilizate | | | | |
| | Ciprofloxacin | 100 mg | | 302 | 1.00 |
| | Solution | | | | |
| | Lactic acid 20% (w/w) | 186 mg | | 413 | 1.37 |
| | 0.1 M hydrochloric acid solution | 0.42 ml | | 142 | 0.47 |
| | Glucose | 25.0 g | | | |
| | Water | ad | 500.0 ml | | |
| | Prepare solution ready for use y dissolving the lyophilizate in the solution | | | | |
| 88 | Lyophilizate | | | | |
| | Ciprofloxacin lactate | 63.6 mg | | 151 | 1.00 (containing an equimolar amount of lactic acid) |
| | Solution | | | | |
| | Lactic acid 0.2% (w/w) | 32.5 g | | 721 | 4.77 |
| | Mannitol | 16.7 g | | — | — |
| | 0.2 M sodium hydroxide solution | 0.89 ml | | 178 | |
| | Water | ad | 333 ml | | |
| | Prepare solution ready for use by dissolving the lyophilizate in the solution | | | | |
| 89 | Lyophilizate | | | | |
| | Ciprofloxacin | 200 mg | | 604 | 1.00 |
| | Sodium chloride | 900 mg | | | |
| | Solution | | | | |
| | Lactic acid 2% (w/w) | 3.330 g | | 715 | 0.18 |
| | Hydrochloric acid | 3.3 mg | | 90 | 0.15 |
| | Water | ad | 100.0 ml | | |
| | Prepare solution ready for use by dissolving the lyophilizate in the the solution | | | | |
| 90 | Lyophilizate | | | | |
| | Ciprofloxacin lactate | 222 mg | | 604 | 1.00 (containing an equimolar amount of lactic acid) |
| | Glucose | 12.5 g | | | |
| | Solution | | | | |
| | Lactic acid 20% (w/w) | 100 mg | | 222 | 0.37 |
| | Hydrochloric acid | 10.4 mg | | 284 | 0.47 |
| | Water | ad | 250 ml | | |
| | Prepare solution ready for use by dissolving the lyophilizate in the solution | | | | |
| 91 | Lyophilizate | | | | |
| | Ciprofloxacin lactate | 222 mg | | 604 | 1.00 (containing an equimolar amount of lactic acid) |
| | Solution | | | | |
| | Sodium chloride | 1.80 g | | — | — |
| | Water | ad | 200 ml | | |
| | Prepare solution ready for use by dissolving the lyophilizate in the solution | | | | |
| 92 | Lyophilizate | | | | |
| | Ciprofloxacin lactate | 222 mg | | 604 | 1.00 (containing an equimolar amount of lactic acid) |
| | Lactic acid | 10 mg | | 111 | 0.18 |
| | Mannitol | 5.0 g | | | |
| | Solution | | | | |
| | Water | | 100.0 ml | | |
| | Prepare solution ready for use by dissolving the lyophilizate in the solution | | | | |
| 93 | Lyophilizate | | | | |
| | Lyophilisate from Example 92 | | | | |
| | Solution | | | | |
| | Water | | 200.0 ml | | |

| Examp. No. | Formulation | | | Micromole | R |
|---|---|---|---|---|---|
| | Prepare solution ready for use by dissolving the lyophilizate in the solution | | | | |
| 94 | Lyophilizate | | | | |
| | Ciprofloxacin lactate | 636 mg | | 1510 | 1.00 (containing an equimolar amount of lactic acid) |
| | Lactic acid | 32 mg | | 355 | 1.24 |
| | Solution | | | | |
| | Ringer lactate solution: | | 100 ml (for example Ringer lactate DAB 7 supplied by Braun Melsungen Rote Liste 1985 No. 51013) | | |
| | Prepare solution ready for use by dissolving the lyophilizate in the solution | | | | |
| 95 | Lyophilizate | | | | |
| | Lyophilizate from Example 94 | | | | |
| | Solution | | | | |
| | Sodium chloride | 0.9 g | | | |
| | Water | ad | 100.0 ml | | |
| | Prepare solution ready for use by dissolving the lyophilzate in the solution | | | | |
| 96 | Lyophilizate | | | | |
| | Lyophilizate from Example 94 | | | | |
| | Solution | | | | |
| | Glucose | 12.5 g | | | |
| | Water | ad | 250.0 ml | | |
| | Prepare solution ready for use by dissolving the lyophilizate in the solution | | | | |
| 97 | Lyophilizate | | | | |
| | Lyophilizate from Example 94 | | | | |
| | Solution | | | | |
| | Solution for supplying amino acids: | | 500 ml (for example aminoplasmal LS-5 electrolyte-free, supplied by Braun Melsungen, Rote Liste 1985 No. 51238) | | |
| | Prepare solution ready for use by dissolving the lyophilizate in the solution | | | | |
| 98 | Lyophilizate | | | | |
| | Cipropfloxacin | 100 mg | | 302 | 1.00 |
| | Solution | | | | |
| | Malic acid | 41 mg | | 306 | 1.01 |
| | Sorbitol | 2.5 g | | | |
| | Water | ad | 50.0 ml | | |
| | Prepare solution ready for use by dissolving the lyophilizate in the solution | | | | |
| 99 | Lyophilizate | | | | |
| | Ciprofloxacin lactate | 127 mg | | 302 | 1.00 (containing an equimolar amount of lactic acid) |
| | Solution | | | | |
| | Lactic acid 20% (w/w) | 12 mg | | 27 | 1.09 |
| | Propionic acid | 45 mg | | 608 | 2.01 |
| | Sodium chloride | 4.5 g | | | |
| | Water | ad | 500 ml | | |
| | Prepare solution ready for use by dissolving the lyophilizate in the solution | | | | |

It will be understood that the specification and examples are illustrative but not limitative of the present invention and that other embodiments within the spirit and scope of the invention will suggest themselves to those skilled in the art.

What is claimed is:

1. An aqueous infusion solution comprising 0.015 to 0.5 g of an active compound, said active compound being 1-cyclopropyl-6-fluoro-1,4-dihydro-4-oxo-7-(1-piperazinyl)-quinoline-3-carboxylic acid, per 100 ml of aqueous solution and an amount of at least one physiologically tolerated acid which suffices to dissolve the active compound, wherein there are 1.33 to 2.2 moles per mole of active compound, of the physiologically tolerated acid, the physiologically tolerated acid being selected from the group consisting of hydrochloric acid, methanesulphinc acid, propionic acid, succinic acid, glutaric acid, citric acid, fumaric acid, maleic acid, tartaric acid, glutamic acid, gluconic acid, glucuronic acid, galacturonic acid, ascorbic acid, phosphoric acid, nitric acid, acetic acid, malic acid, L-aspartic acid and lactic acid.

2. An infusion solution according to claim 1, containing a mixture of physiologically tolerated acids to dissolve the active compound.

3. An infusion solution according to claim 1, wherein the physiologically tolerated acid is selected from the group consisting of lactic acid, hydrochloric acid and mixtures of lactic acid and hydrochloric acid.

4. An infusion solution according to claim 1, containing 1.33 to 1.50 mols of lactic acid per mol of active compound.

5. An infusion solution according to claim 1, having a pH from 3 to 5.2.

6. An infusion solution according to claim 1, having a pH from 3.6 to 4.7.

7. An infusion solution according to claim 1, having a pH from 3.9 to 4.5.

8. An infusion solution according to claim 1, having a pH from 4.1 to 4.3.

9. An infusion solution according to claim 1, which is substantially isotonic.

10. An infusion solution according to claim 1, containing 1.33 to 2.2 mols of lactic acid and 0.0 to 0.80 mol of hydrochloric acid per mol of active compound, and relative to 100 ml of solution, 0.6 to 2.2 g of NaCl.

11. An infusion solution according to claim 1, containing 1.33 to 1.4 mols of lactic acid and 0.0 to 0.80 mol of hydrochloric acid per mol of active compound, and relative to 100 ml of solution, 0.75 to 1.2 g of NaCl.

12. An infusion solution according to claim 1, present in a container in from 40 to 600 ml.

13. An infusion solution according to claim 1, wherein the physiologically tolerated acid is lactic acid.

* * * * *